(12) United States Patent
Baumann et al.

(10) Patent No.: US 7,533,991 B2
(45) Date of Patent: May 19, 2009

(54) OPHTHALMOLOGICAL APPLIANCE COMPRISING AN EYE TRACKER

(75) Inventors: Oliver Baumann, Aalen (DE); Michael Claus, Aalen (DE); Axel Doering, Jena (DE); Ingo Koschmieder, Jena (DE); Thomas Schulze, Erlangen (DE); Bernd Spruck, Moegglingen (DE)

(73) Assignee: Carl Zeiss Meditec AG, Jena (DE)

( * ) Notice: Subject to any disclaimer, the term of this patent is extended or adjusted under 35 U.S.C. 154(b) by 261 days.

(21) Appl. No.: 10/535,730

(22) PCT Filed: Nov. 13, 2003

(86) PCT No.: PCT/EP03/12673

§ 371 (c)(1),
(2), (4) Date: Jan. 3, 2006

(87) PCT Pub. No.: WO2004/045401

PCT Pub. Date: Jun. 3, 2004

(65) Prior Publication Data

US 2006/0152676 A1    Jul. 13, 2006

(30) Foreign Application Priority Data

Nov. 21, 2002   (DE)   ................. 102 54 369

(51) Int. Cl.
*A61B 3/10* (2006.01)
(52) U.S. Cl. .................. 351/214; 351/209; 351/221
(58) Field of Classification Search ................ 351/214, 351/212, 205, 206, 239, 243, 246, 247, 221, 351/208, 209
See application file for complete search history.

(56) References Cited

U.S. PATENT DOCUMENTS

| | | | |
|---|---|---|---|
| 5,943,118 A * | 8/1999 | Koschmieder et al. | ...... 351/243 |
| 6,145,990 A | 11/2000 | Uchida | |
| 6,220,706 B1 | 4/2001 | Foley | |
| 6,631,990 B2 * | 10/2003 | Schippert et al. | ............ 351/214 |

(Continued)

FOREIGN PATENT DOCUMENTS

DE    101 51 314    4/2003

(Continued)

*Primary Examiner*—Hung X Dang
(74) *Attorney, Agent, or Firm*—Reed Smith LLP

(57) ABSTRACT

The present invention is directed to an arrangement and a method for eye examination and/or for determining biometric eye data in which the movement of the eyes is compensated through the use of an eye tracker unit. The arrangement comprises a controllable digital illumination unit and an observation system which are arranged on separate supporting arms. A central control unit has connections to an image recording unit, an optical imaging system, an eye tracker unit and an output unit. Further, transmitter elements and/or actuating drives are provided at the separate supporting arms, at the zoom system and at the magnification changer. The examination can be adapted in an optimal manner to the task at hand by means of the structured illumination patterns that can be generated in a variable manner. Detection of all adjusting parameters relevant for recording can be used for calculations and for reconstructing the pertinent observation conditions. In case of repeated examinations for determining changes, e.g., during the recovery process following eye surgery, the regions can be found again in a simple manner and examined under exactly the same conditions.

16 Claims, 2 Drawing Sheets

U.S. PATENT DOCUMENTS

2002/0060778 A1    5/2002   Su et al.

FOREIGN PATENT DOCUMENTS

| EP | 1 088 511 | 4/2001 |
|---|---|---|
| EP | 1 327 412 | 7/2003 |
| WO | WO 99/27412 | 6/1999 |
| WO | WO 99/56611 | 11/1999 |

\* cited by examiner

OPHTHALMOLOGICAL APPLIANCE COMPRISING AN EYE TRACKER

CROSS-REFERENCE TO RELATED APPLICATION

This application claims priority of International Application No. PCT/EP2003/012673, filed Nov. 13, 2003 and German Application No. 102 54 369.0, filed Nov. 21, 2002, the complete disclosures of which are hereby incorporated by reference.

BACKGROUND OF THE INVENTION a) Field of the Invention

The present invention is directed to an arrangement and a method for eye examination and for determining eye data through measurement technique in which the movement of the eyes is compensated through the use of an eye tracker unit so that results are achieved faster and with increased measuring accuracy.

b) Description of the Related Art

There are numerous ophthalmologic devices known from the prior art that can be used to enable determined measurement tasks on the eye and to find and examine points or regions in the eye.

Patent EP 1 088 511, for example, describes an ophthalmologic device which has a positioning unit for orientation of the measuring unit with respect to the eye to be examined. For this purpose, a detection unit which determines the relative position of the measurement unit with respect to the eye and monitors this position during measurement is provided. The determined measurement values are stored or rejected depending on the eye position determined by the detection unit. In this way, only measurements that were recorded when the eye was accurately positioned are processed and stored. This solution is disadvantageous due to the fact that the measurement unit of the ophthalmologic device must be roughly oriented by the user by means of a joystick at the start of the examination.

An automatically aligning optometric measurement device and the method for its use are described in U.S. Pat. No. 6,145,990. This solution has means for projecting a light mark on the eye, means for evaluating corneal reflex images, and means for controlling the actuating drives for exact positioning of the optometric measurement device. Positioning is carried out in all three coordinate directions for the first eye and then for the second eye based on the position of two light marks relative to one another, these light marks being generated from the corneal reflex image.

In the solution described in U.S. Pat. No. 6,220,706, the position of the eyes is likewise determined by illuminating the eyes and subsequently evaluating the reflected beam. For this purpose, two pairs of radiation emitters and photodetectors are arranged in such a way that the photodetectors can receive the radiation that is emitted by the respective associated radiation emitter and reflected by the eye. A controller analyzes the data of the photodetectors, which are constructed as 4-quadrant photodetectors, in order to determine the exact position of the eye. This technical solution determines, in particular, the focus position, i.e., the exact distance of the corneal vertex from the optics of the device.

While the known technical solutions are capable of aligning to the eye of the patient, finding determined points or regions still depends upon the skill of the operator. The duration of an examination, e.g., for monitoring the healing process after a surgical procedure, depends upon how quickly the operator finds the determined point or region in question. Further, it is not possible to carry out an examination under consistent conditions, so that the healing process likewise depends upon the subjective assessment of the operator.

OBJECT AND SUMMARY OF THE INVENTION

It is the primary object of the present invention to develop an ophthalmologic device for measuring anatomical structures by means of variably structured illumination patterns and a method for controlling this device by which eye movements can be compensated by tracking and which makes possible shorter treatment times, thereby minimizing stress on the patient, by means of finding determined points or regions again in a simple and rapid manner, e.g., to monitor the healing process after a surgical procedure.

According to the invention, this object is met in accordance with the invention, by an ophthalmologic device with eye tracker unit comprising a controllable illumination unit and an observation system. The illumination and observation system are arranged on separate supporting arms. The device further comprises an image recording unit, an optical imaging system and an output unit, all being connected to a central control unit.

The ophthalmologic device for determining biometric data of an eye has many applications both in medicine and in optometry. A significant savings in time is achieved due to the illuminated tracking and movement compensation in eye movements. Some ophthalmologic devices already use eye tracker units so that no significant increase in or further complication of technical apparatus is required.

The invention will be described more fully in the following with reference to an embodiment example.

DESCRIPTION OF THE PREFERRED EMBODIMENTS

Figure 1:
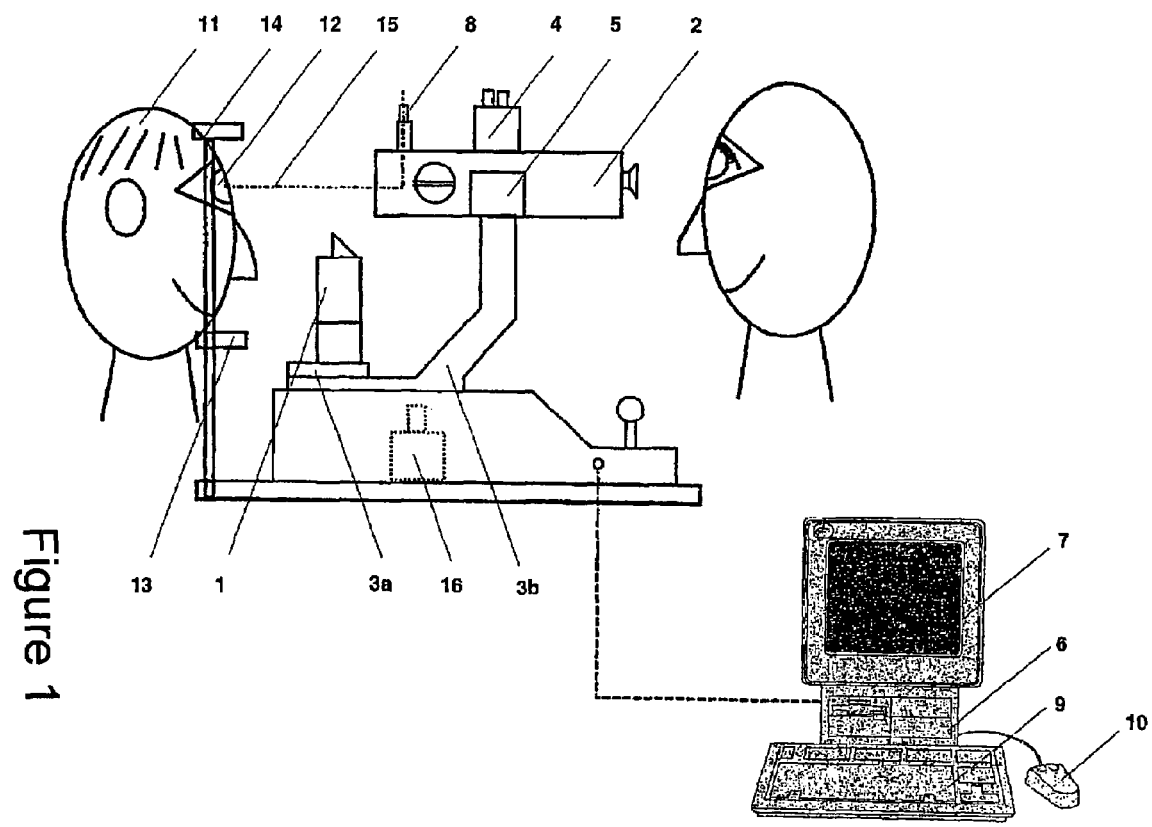
FIG. 1 is a schematic view of the ophthalmologic device.

An ophthalmologic device with an eye tracker unit is shown schematically in FIG. 1 and comprises a digitally controllable illumination unit 1 and a stereo microscope which serves as an observation system 2 which are arranged on separate supporting arms 3a and 3b so as to be swivelable independent of one another. Angle transmitters are arranged at the supporting arms 3a and 3b. The image recording unit 4 is a digital high-resolution camera with a high image rate. The illumination unit 1 can comprise a light source, an optoelectronic component with individually controllable pixel elements, and a projection unit. Microdisplays, e.g., DMD, LCOS, LCD, or LED types with individually controllable pixel elements, can be used as optoelectronic component. These microdisplays serving as illumination unit 1 are preferably synchronized with the image rate of the image recording unit 4 and are connected to an optical imaging system 5 and central control unit 6 for detection, processing and storage of data. The central control unit 6 has a user interface and has connections to a monitor 7 and/or printer serving as an output unit and to an eye tracker unit 8 as well as to parameter transmitting components. The eye tracker unit 8 is advisably coupled with the optical axis 15 of the stereo microscope serving as observation system 2 by means of a mirror so that a parallax need not be taken into account.

The image recording unit 4 advantageously has a device for inclining the camera chip relative to the optical axis 15 for Scheimpflug correction and is also capable of recording image sequences. The user interface of the control unit 6 has input devices such as keyboard 9, mouse 10, trackball, joystick, or the like, by means of which different control modes and evaluating modes can be called up.

In the method, the eye 12 of the patient 11 to be examined is brought to a fixed position by means of the provided chin rest 13 and forehead support 14. The eye tracker unit 8, which comprises, for example, a camera and IR illumination, supplies signals which exactly define the position of the pupil center. These coordinates define the position of the patient's eye 12 relative to the eye tracker unit 8 and therefore also relative to the optical axis of the ophthalmologic device itself. When the patient's eye 12 moves, a corresponding reference value is generated by the central control unit 6 with respect to amount and direction for tracking. The difference between the optical axis of the eye 12 and the optical axis 15 of the ophthalmologic device is zeroed by relative tracking of the illumination pattern on the microdisplay that is used and continuous monitoring by the eye tracker unit 8. This is possible because the eye tracker unit 8 has a high measurement repetition rate and supplies the exact coordinates of the pupil center multiple times per second. The tracking is carried out in a purely electrical, optical manner by means of the pixel elements of the display without moving the device or its parts. By means of projecting the quasi-movable pattern, the image is tracked on the eye 12. In this way, for example, a virtual coordinate system can be 'fixedly connected' to a determined point on the eye, e.g., the pupil center. This coordinate system will track the eye movement online so that it has the appearance of being 'fixedly connected' to the eye.

A wide variety of illumination patterns are projected on the eye 12 for the examination and measurement of the eye 12. These illumination patterns are shifted in direction and amount, rotated around freely selectable reference points and are freely selectable with respect to their radiating direction relative to the optical axis 15. The light marks and/or coordinate systems 17 projected on the eye 12 can follow the movement of the eye by means of the eye tracker unit 8. For this purpose, light marks of any shape can be generated and positioned and 'anchored' relative to the eye 12 by means of a joystick or a mouse 10. These different illumination patterns are maintained stationary with respect to their position on the eye 12 in spite of eye movement by means of real-time tracking in that the eye tracker unit 8 carries out a continuous detection of the pupil. The tracking based on this detection by the eye tracker unit 8 is carried out by means of the illumination unit 1, whose optoelectronic microdisplay is dimensioned in such a way that the eye region to be examined can be illuminated in its entirety. Accordingly, the tracking of the illumination structures is carried out without any mechanically moving parts.

For example, illumination patterns that are suitable for determining the surface shape or the thickness of the cornea, e.g., grids, lines, stars, rings, or the like, are projected on the eye at varying radiating angles. All of the relevant adjusting parameters (angle, line thickness, brightness, distances, etc.) are documented and stored together with the recording. Calculation of the biometric data is carried out subsequently by means of triangulation while taking into account the refracting media of the eye. But the parameters of the eye, e.g., the radius and thickness of the cornea at different locations, the extension of the anterior chamber and eye lens, or the diameter and extension of the pupil or iris, can also be determined.

Searching of illumination patterns in digital images can be carried out by means of differential image recordings in that two images which are recorded in direct succession in time with a change exclusively in the illumination pattern are subtracted from one another and all interfering spatially fixed image information such as reflections are eliminated. In so doing, the illumination pattern is shifted by a slight amount in any direction only in an electrical optical manner.

The signal of the eye tracker unit 8 can also be used for marking a region or location and finding it again. The eye tracker unit 8 preferably detects the eye 12 to be examined up to the edge of the iris, which corresponds to a diameter of about 12 mm. The different illumination patterns for identifying and marking regions of interest (ROI) 18 are positioned and held stationary online on the eye 12 and monitor 7 or, after the relevant position parameters of the system have been stored, can be used later for finding exactly this ROI 18 again. For this purpose, the data of the image recording unit 4 are stored for later use.

The settings are stored by the angle transmitters arranged at the swiveling arms 3a and 3b of the illumination unit 1 and observation system 2. The angle transmitters preferably operate digitally. For the purpose of a simple and fast reconstruction of the stored illumination conditions and observation conditions, it is advisable that the swiveling arms 3a and 3b, respectively, have in addition an automatic actuating drive for adjusting the previously stored values. The relevant user parameters and settings of the system can be determined or found again either in a partly automatic manner by the user or fully automatically by means of the actuating drive.

Figure 2:
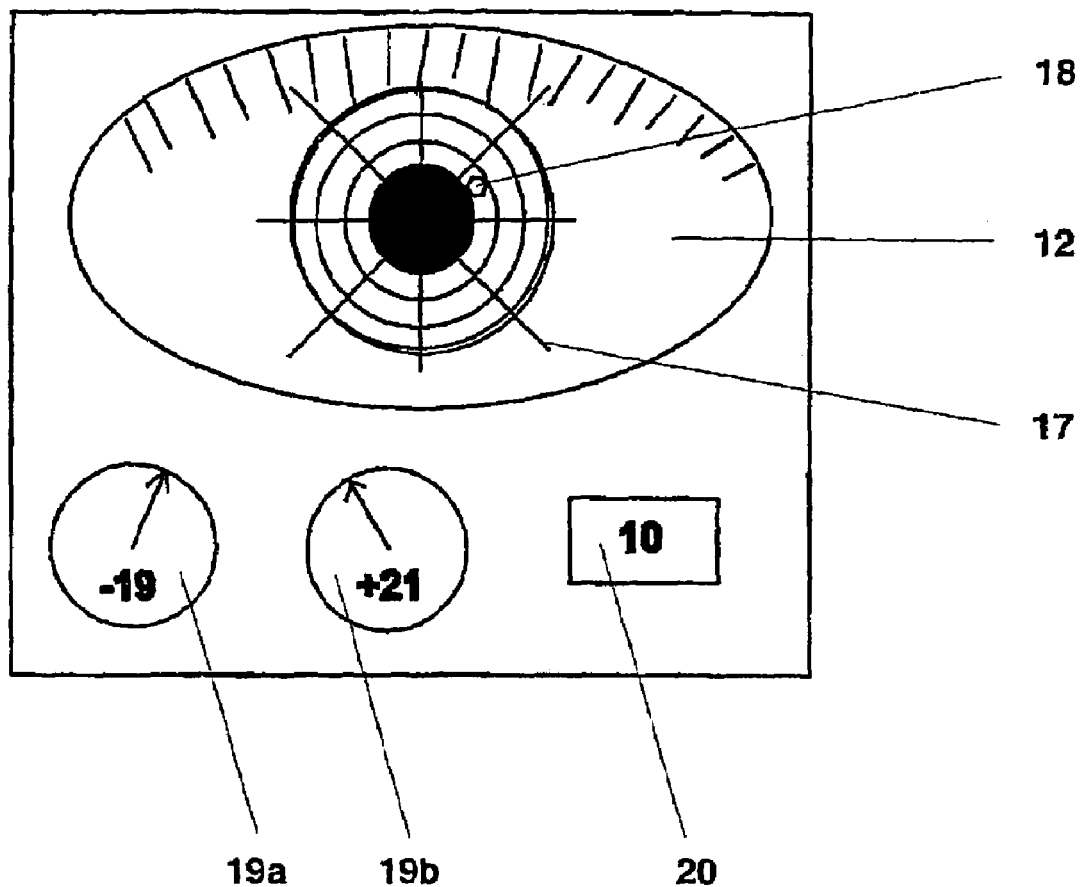
FIG. 2 shows a possible monitor image or live image with a marked ROI.

It is useful to display additional parameters such as angle settings for illumination 19a and observation 19b, the magnification stage 20 of the observation system, etc. in the viewer of the observation system and/or in the monitor picture. In this connection, FIG. 2 shows a possible monitor image or live image with a flagged ROI.

Further automation of the examination sequences is possible when ophthalmologic examination devices of this kind have means for automatically positioning on the eye to be examined after automatic eye detection. Numerous technical solutions are known from the cited art for this purpose.

The solution proposed with the ophthalmologic device according to the invention for examining and determining biometric data of an eye and the method for use of this device improves, simplifies and accelerates the examination and determination of the biometric data of an eye for the operator and for the patient. The examination can be adapted in an optimal manner to the task at hand, e.g., measurement of the anatomical factors on and in the eye, by means of the structured illumination patterns that can be generated in a variable manner. Detection of all adjusting parameters relevant for recording can be used for the subsequent calculation of the triangulation on one hand and for reconstructing the pertinent observation conditions on the other hand. The movement of the eyes can be compensated and suppression of interference and recording quality can be significantly improved by electrical, optical tracking of the projection pattern on the microdisplay. Sources of interference in the recording can be eliminated by differential image methods. In case of repeated examinations for determining changes, e.g., during the recovery process following eye surgery, the regions of interest (ROI) can be found again and examined in a simple manner. In this connection, it is particularly advantageous that an examination of the location in question (ROI) can be carried out under exactly the same conditions based on the stored data. Changes during the recovery process can be determined faster and more precisely when the ophthalmologic device has automatic actuating drives which make it possible to find and position the eye automatically based on the stored adjusting parameters.

The present invention can advantageously be used in connection with an arrangement and a method for determining the biometric data of an eye with structured illumination and subsequent triangulation based on manual or stored process sequences. The measuring accuracy and suppression of interference variables during measurements can be substantially improved by compensating for the eye movements of the patient. The invention can also be used, for example, to project structures on the eye by means of electronic, software-controlled illumination devices. These devices are aligned to the eye, 'fixedly connected' to a determined position of the eye, e.g., the pupil center, and the movement of the eye can accordingly be tracked online. Movements of the eye are compensated so that the structure is shown at a fixed position relative to the eye. Another application is, for example, automatically finding again the position marked in the preceding examination on or in the eye and marking or measuring this position again. Further, an arrangement and/or a method based on this principle can be used to align the entire ophthalmologic device relative to the eye position.

While the foregoing description and drawings represent the present invention, it will be obvious to those skilled in the art that various changes may be made therein without departing from the true spirit and scope of the present invention.

REFERENCE NUMBERS 1 illumination unit
2 observation system
3a, 3b supporting arms
4 image recording unit
5 optical imaging system
6 central control unit
7 monitor
8 eye tracker unit
9 keyboard
10 mouse
11 patient
12 eye to be examined
13 chin rest
14 forehead support
15 optical axis
16 actuating drive
17 coordinate system
18 region of interest (ROI)
19a angle adjustments for illumination
19b angle adjustments for observation
20 magnification stage

The invention claimed is:

1. An ophthalmologic device comprising:
an eye tracker unit for compensating for movement of the eye to be examined;
a controllable illumination unit and an observation system;
said illumination unit and observation system being arranged on separate supporting arms;
said device further comprising an image recording unit, an optical imaging system and an output unit, all being connected to a central control unit.

2. The ophthalmologic device according to claim 1, wherein the separate supporting arms of the illumination unit and of the observation system are swivelable independent of one another and have transmitter elements.

3. The ophthalmologic device according to claim 1, further comprising a zoom system and a magnification changer and wherein transmitter elements are additionally arranged at said zoom system and at said magnification changer.

4. The ophthalmologic device according to claim 1, wherein the eye tracker unit has a measurement repetition rate and an image area which detects the eye to be examined until the edge of the iris, and the optical axis of the eye tracker unit corresponds to that of the observation system.

5. The ophthalmologic device according to claim 1, wherein said image recording unit is a digital high-resolution camera having a high image rate.

6. The ophthalmologic device according to claim 5, wherein the image rate of the digital high-resolution camera operates synchronous with an image rate of a digital illumination unit.

7. The ophthalmologic device according to claim 1, wherein the central control unit has a user interface with conventional input devices and has different control modes and evaluating modes.

8. The ophthalmologic device according to claim 1, wherein the output unit is a monitor or printer.

9. The ophthalmologic device according to claim 1, wherein the swiveling arms of the illumination unit and observation device have an angle transmitter or an actuating drive.

10. The ophthalmologic device according to claim 1, further comprising a zoom system and a magnification changer and wherein the zoom system and the magnification changer have a transmitter element or an actuating drive.

11. The ophthalmologic device according to claim 1, wherein parameters of an illumination pattern are stored by the central control unit and displayed in a display unit on the monitor or in the viewer or eyepiece.

12. A method for operating an ophthalmologic device comprising the steps of:
providing an eye tracker unit for compensating for movement of the eye to be examined;
generating different illumination patterns and projecting them on the eye;
shifting said illumination patterns in direction and amount, rotating them around freely selectable reference points, and scaling them with respect to size and line width;
said illumination patterns being freely selectable with respect to their radiating direction relative to the optical axis and being held so as to be fixed at a point on the eye in real time by tracking without movement.

13. The method according to claim 12, wherein different illumination patterns for identifying and marking regions of interest (ROI) can be held stationary online on the eye and monitor and, after the relevant position parameters of the system have been stored, can be used later for finding the ROI again.

14. The method according to claim 12, wherein additional parameters can be stored in addition to the relevant position parameters for finding the ROI again.

15. The method according to claim 12, wherein suitable scaled illumination patterns are projected on the eye at variable radiating angles and calculation of the biometric data is carried out by triangulation while taking into account refracting media of the eye.

16. The method according to claim 12, wherein searching of illumination patterns in digital images can be carried out by differential image recordings in that two or more images which are recorded in direct succession in time with a change exclusively in the illumination pattern are subtracted from one another and all interfering spatially fixed image information is accordingly eliminated.

* * * * *